United States Patent [19]
Yano et al.

[11] Patent Number: 5,298,246
[45] Date of Patent: Mar. 29, 1994

[54] STABLE PHARMACEUTICAL COMPOSITION AND METHOD FOR ITS PRODUCTION

[75] Inventors: Yoshiaki Yano, Kakogawa; Shigeki Masuda, Takasago; Takayoshi Hidaka, Kobe, all of Japan

[73] Assignee: Kanegafuchi Kagaku Kogyo Kabushiki Kaisha, Osaka, Japan

[21] Appl. No.: 815,189

[22] Filed: Dec. 31, 1991

[51] Int. Cl.$^5$ .................... A61K 37/48; A61K 37/22; A61K 37/00; A61K 37/12
[52] U.S. Cl. .................... 424/94.1; 424/450; 424/491; 514/24; 514/678
[58] Field of Search .................... 424/94.1, 450, 94.3, 424/491; 514/21, 678

[56] References Cited

U.S. PATENT DOCUMENTS

| | | | |
|---|---|---|---|
| 4,663,161 | 5/1987 | Mannino et al. | 424/450 |
| 4,766,046 | 8/1988 | Abra et al. | 424/450 |
| 4,837,028 | 6/1989 | Allen | 424/450 |
| 4,920,016 | 4/1990 | Allen et al. | 424/94.3 |
| 4,994,496 | 2/1991 | Repasky et al. | 424/94.3 |

FOREIGN PATENT DOCUMENTS

| | | |
|---|---|---|
| 0069399 | 1/1983 | European Pat. Off. |
| 0306971 | 2/1989 | European Pat. Off. |
| 0385445 | 9/1990 | European Pat. Off. |
| 0042616 | 3/1982 | Japan .................... 424/94.1 |
| 3-165833 | 7/1991 | Japan . |
| 3-251143 | 11/1991 | Japan . |

OTHER PUBLICATIONS

Kirk-Othmer *Encyclopedia of Chemical Technology*, 3rd ed., vol. 8, 1979, pp. 900-912, 916-924.
Drug Delivery System, vol. 5, No. 2, pp. 61-64 (1990).
Liu et al, Yakugaku Zasshi, vol. 111, No. 9, pp. 510-515 (1991).
Kanamori et al, Yakuzaigaku, vol. 45, No. 2, pp. 119-126 (1985).
McPherson et al, Journal of Dairy Research, vol. 50, pp. 107-133 (1983).
Chemical Abstracts, vol. 114, No. 12, Abstract No. 108805c (1991).

*Primary Examiner*—Douglas W. Robinson
*Assistant Examiner*—Kristin Larson
*Attorney, Agent, or Firm*—Birch, Stewart, Kolasch & Birch

[57] ABSTRACT

The present invention is directed to a stable pharmaceutical composition wherein the absorbability of a lipophilic drug which is insoluble or practically insoluble in water or another drug such as a bioactive peptide in oral administration has been improved to such extent that a high level of blood concentration can be retained, and to a method for producing such a stable pharmaceutical composition. The pharmaceutical composition of the present invention offers improvements in the absorbability, for example, a high level of blood concentration can be retained for a long time in oral administration because it is highly resistant to lipase. Also, the pharmaceutical composition is highly safe because the emulsifier used is derived from mammalian milk.

8 Claims, 10 Drawing Sheets

STABLE PHARMACEUTICAL COMPOSITION AND METHOD FOR ITS PRODUCTION

FIELD OF THE INVENTION

The present invention relates to a stable pharmaceutical composition wherein the absorbability of a lipophilic drug, which is insoluble or practically insoluble in water or another drug such as a bioactive peptide, in oral administration is improved and to a method for its production.

BACKGROUND OF THE INVENTION

With respect to lipophilic drugs which are insoluble or practically insoluble in water, it is difficult to retain a sufficient blood concentration level thereof when they are administered orally because their absorbability is low. For this reason, administration of these drugs depends on oral mass administration or injection, which poses a major clinical problem and a great burden on patients. If the absorption speed, absorption rate and other factors of these drugs in oral administration are improved, treatment by oral administration will be possible and prior burdens on patients will be reduced; therefore, development of such an orally administrable preparation of a lipophilic drug which is insoluble or practically insoluble in water is urgently demanded by those skilled in the art.

For example, ubidecarenone, which is now clinically widely used as a pharmaceutical effective for improvement in coronary function, is well known to be low in absorbability upon oral administration because it is practically insoluble in water. When ubidecarenone is administered orally, its retention is transient in many tissues except for the tissues where ubidecarenone is liable to accumulate, such as the liver, spleen and adrenal; therefore, ubidecarenone needs to be administered in a large amount to ensure a sufficient level of pharmacological activity. In this case, frequent mass administration poses a great burden on the patients, even in oral administration, and is undesirable also from the viewpoint of prevention of adverse effects associated with mass administration.

With the recent progress of pharmaceutical preparation technology, this problem has been investigated from various viewpoints, including attempts to improve the absorbability of these lipophilic drugs by orally administering them after dissolution or emulsification dispersion using surfactants, oils and fats, or after such preparations. However, a satisfactory effect with such methods cannot always be obtained. Also, attention should be given to the use of surfactants and other additives from the viewpoint of safety. For example, nonionic surfactants such as polyoxyethylene hardening castor-oil and polyoxyethylene sorbitan monooleate have been used, but their pharmaceutical use in practical situations is often avoided since they pose problems such as hemolysis, mucosal irritation and mucosal deficiency.

On the other hand, safer synthetic surfactants such as fatty acid esters of polyglycerol and fatty acid esters of glycerol have recently been widely used; however, there are new demands for the development of natural type emulsifiers whose emulsifying capability is equivalent to, or higher than, that of the safer synthetic surfactants and whose overall safety are very high. Improvement in the absorbability of these lipophilic drugs by the use of any useful pharmaceutical additives will offer clinically significant utility.

As for bioactive peptides, the route of their administration has usually been limited to injection. This is because bioactive peptides in oral administration cannot be absorbed via the enteric canal due to the fact that most of them have a high molecular weight, and because their absorption into blood cannot be expected due to hydrolysis by proteolytic enzymes in the digestive tract. However, their administration by injection poses a great burden on patients. Under these conditions, various attempts have recently been made to develop orally administrable preparations of bioactive peptides, but there are no preparations which ensure good absorption into blood.

On the other hand, a recent report of the studies of drug delivery system suggests that the bovine milk fat globule membrane generally serves well as a very safe natural emulsifier [Drug Delivery System, 5 (2), 61-64, 1990]. The bovine milk fat globule membrane, known as a structural lipoprotein consisting mainly of lipid and protein, contains fat globules having a diameter of 0.1 to 10 $\mu$m at the number of $3.6 \times 10^9$ per ml of bovine milk on average. It is also known that these fat globules can maintain a stable emulsion state by the emulsive action of this bovine milk fat globule membrane. There are a large number of reports on biochemical studies of the structures and compositions of the bovine milk fat globule membrane. However, the grain size distribution of fat globules is rather wide; there are no reports on attempts to determine which grain size fraction is the most effective on the improvement of absorbability of lipophilic drugs and bioactive peptides when they are emulsified with the bovine milk fat globule membrane.

SUMMARY OF THE INVENTION

It is an object of the present invention to provide a stable pharmaceutical composition wherein the absorbability of a lipophilic drug which is insoluble or practically insoluble in water or another drug, such as a bioactive peptide, upon oral, administration has been improved to such extent that a high blood concentration level thereof can be obtained.

It is another object of the present invention to provide a method for producing such a stable pharmaceutical composition.

With the aim of improving the absorbability of lipophilic drugs which are insoluble or practically insoluble in water or drugs such as bioactive peptides in oral administration, the inventors made investigations and found that the absorbability of these drugs can be improved by administering an emulsion with high emulsification stability containing a lipophilic drug which is insoluble or practically insoluble in water or a bioactive peptide, obtained by fractionally purifying oil-in-water emulsion grains prepared using a fat globule membrane for mammalian milk such as bovine milk fat globule membrane as an emulsifier, or a preparation prepared from said emulsion. The inventors made further investigations based on this finding, and developed the present invention.

Accordingly, the present invention essentially relates to a stable pharmaceutical composition which contains a drug emulsified with a fat globule membrane of mammalian milk wherein the emulsified drug is obtained from a grain size fraction containing a high density of lipid microspheres with high emulsification stability. The present invention also relates to a method for producing a stable pharmaceutical composition wherein a drug is emulsified with a fat globule membrane of mammalian milk and then centrifuged under at least two different sets of conditions to fractionally purify the desired grain size fraction.

DETAILED DESCRIPTION OF THE INVENTION

Figure 1:
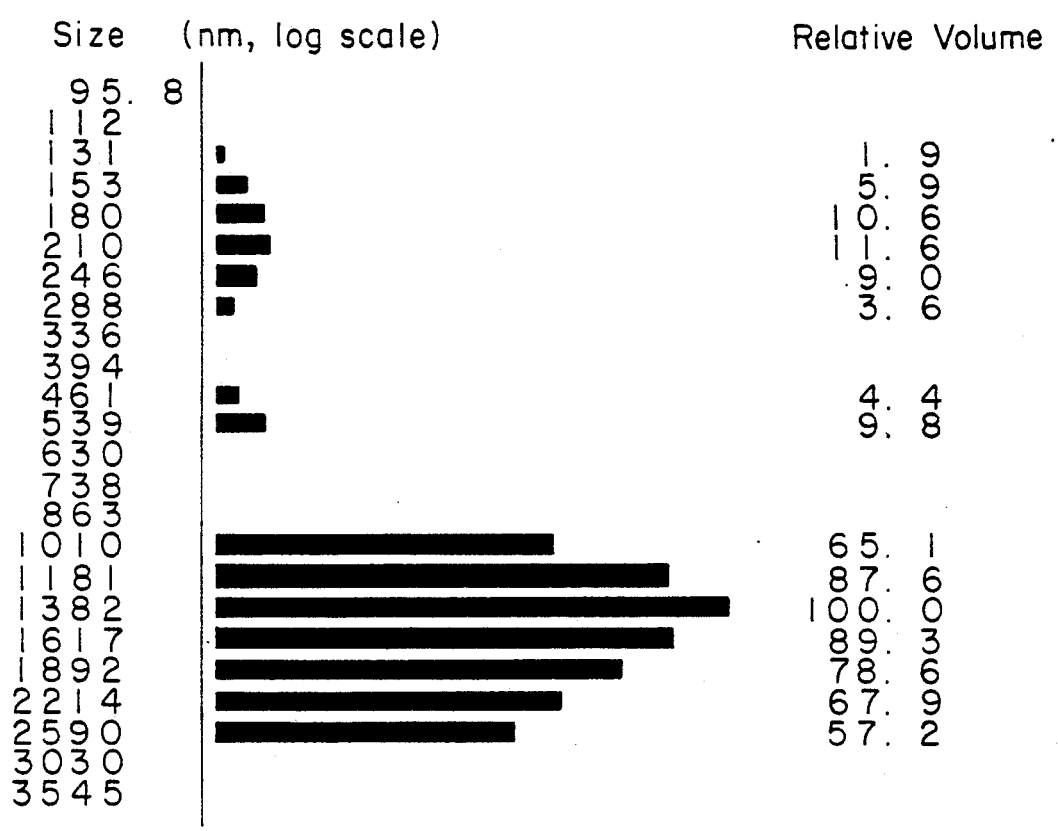
FIG. 1 shows the results of the volumetric analysis of the grain size of the emulsion obtained in Example 1.

The subject drugs for the present invention include lipophilic drugs which are insoluble or practically insoluble in water and another drug such as a bioactive peptide. Here, lipophilic drugs which are insoluble or practically insoluble in water include substances which are insoluble or practically insoluble in water and soluble in organic solvents and substances which are practically insoluble both in water and in organic solvents. Examples of such lipophilic drugs include ubiquinones such as ubidecarenone, lipophilic vitamins such as vitamin E, steroids such as progesterone, methyltestosterone and hydrocortisone, and the other drugs such as nifedipine, rifampicin and griseofulvin.

In the present invention, any bioactive peptide can be used without limitation, as long as it is normally used as a drug for its bioactivity, including extracts from various tissues, synthetic products, those obtained by gene recombination technology and variants as well as naturally occurring products. Such bioactive peptides include insulin, vasopressin, oxytocin, human chorionic gonadotropin (HCG), human menopausal gonadotropin (HMG), growth hormone, corticotropin, calcitonin, gonadotropic hormone-releasing hormone, thyrotropin-releasing hormone, interferon, erythropoietin, colony stimulating factors (e.g., GM-CSF), epithelial growth factor (EGF), nerve cell growth factor (NGF), urokinase, tissue plasminogen activator, staphylokinase, superoxide dismutase, somatomedin, growth hormone-releasing factor, somatostatin, atrial natriuretic polypeptide, protein C, interleukin, tumor necrosis factor (TNF), lactoferrin, transferrin and immunoglobulin.

The lipophilic drugs which are insoluble or practically insoluble in water and bioactive peptides for the present invention include those used as animal drugs as well as those used in humans.

As stated above, the stable pharmaceutical composition of the present invention contains a drug emulsified with a fat globule membrane of mammalian milk and consists mainly of a grain size fraction containing a high density of lipid microspheres with high emulsification stability. The various drugs mentioned above can be used for the present invention; when using ubidecarenone, for instance, as a lipophilic drug, a ubidecarenone-containing composition is obtained. The fat globule membrane of mammalian milk used for the present invention is not subject to limitation, but it is preferable to use the bovine milk fat globule membrane from the viewpoint of easy availability of the starting material. In the present invention, the grain size fraction containing a high density of lipid microspheres with high emulsification stability has a grain diameter of normally about 1 to 5 μm, preferably about 1 to 3 μm from the viewpoint of emulsification stability and content of drugs. Regarding the term "grain size fraction" we mean (1) with respect to lipid microspheres a particle size fraction obtained by fractionation of lipid microspheres, wherein the lipid microspheres are prepared by emulsifying the drug with a fat globule membrane; and (2) with respect to fat globule membranes of mammalian milk we mean the grain size of fat globules therein.

The method for producing the stable pharmaceutical composition of the present invention comprises emulsification of a drug with a fat globule membrane of mammalian milk and subsequent centrifugation under at least two different sets of conditions to fractionally purify the desired grain size fraction. Specifically, the method is carried out as follows: In the case of a lipophilic drug which is insoluble or practically insoluble in water, said drug is used as is when it is oily at room temperature, or it is used after being dissolved in an appropriate oil or fat causing no protein denaturation when it is a solid. It should be noted, however, that when the drug is a powder even if it is a solid, it can be used as is. Next, to the lipophilic drug, which is oily or in solution in oil or fat, a fat globule membrane of mammalian milk is added. After diluting to an appropriate amount with a physiological isotonic buffer (pH 7.0), the mixture is emulsified by homogenization, sonication or other means to yield an oil-in-water emulsion containing various sizes of lipophilic drug grains. After this operation, centrifugation under at least two different sets of conditions and other fractional purification steps are performed to yield an emulsion containing the lipophilic drug with improved emulsification stability.

In the present invention, any oils and fats can be used without limitation, as long as they can serve as a pharmaceutical additive, such as animal oils, vegetable oils, essential oils, lipids and synthetic oils, but preference is given to sesame oil, peanut oil, triolein and the like from the viewpoint of emulsification stability.

The ratio of the milk fat globule membrane added may be set at any level, as long as it is not less than 1% by weight. Although the emulsification stability, emulsification activity and foam stability of the emulsion can be increased by increasing the amount of milk fat globule membrane, it is added preferable to add the milk fat globule membrane in a ratio of 2 to 8% by weight for practical application. When the amount added is expressed per gram of oil or fat, a sufficient effect is obtained with an amount of about 80 mg when the degree of emulsification is taken into consideration, though it should be not less than about 60 mg. If the amount is lower than about 60 mg, no satisfactory emulsification will be obtained; if the amount is increased to over about 80 mg, the effectiveness will remain unchanged, but so high a level is not economic.

Although the lipophilic drug can be added at high concentrations relative to the oils and fats mentioned above, its concentration varies depending on the kind of the oils or fats used. From the viewpoint of recovery, the lipophilic drug is added at normally about 10 to 50%, preferably about 20 to 30%. Examples of the physiological isotonic buffer (pH 7.0) used include sodium phosphate isotonic buffers.

Although the fat globule membrane of mammalian milk used in the present invention is not subject to limitation, it is preferable to use the bovine milk fat globule membrane as stated above from the viewpoint of easy availability of the starting material. A bovine milk fat globule membrane can easily be prepared by a known method. It is a common practice to centrifuge milk, wash the resulting cream several times and then physically disrupt the fat globules in a churning process [Journal of Dairy Research, 50, 107-133, (1983)]. For emulsification, means in general use in the field of pharmaceutical preparation such as ordinary emulsifying machines including homogenizers and sonicators, can be used. Handling conditions of homogenizers and other instruments, e.g., speed, time and temperature, are selected as appropriate according to the milk fat globule membrane concentration, lipophilic drug concentration, pH and other factors.

Fractional purification by centrifugation used for the method of the present invention is carried out under at least two different sets of conditions, i.e., it usually comprises two processes, namely Process A, in which the grain size fractions smaller than about 1 μm are removed, and Process B, in which the grain size fractions larger than about 5 μm are removed. In Process A, centrifugation is carried out at about 3000 to 4000 rpm (about 1500 to 2500×g), for instance, preferably about 3500 rpm (about 2000×g), for more than about 60 minutes, for instance, the lower layer is removed, and the upper layer is suspended in a sodium phosphate isotonic buffer (pH 7.0). This procedure is repeated in several cycles. As a result of Process A, the emulsion fractions whose grain size is smaller than about 1 μm and whose lipophilic drug content is low are removed. In Process B, centrifugation is carried out at about 500 to 1000 rpm (about 50 to 150×g), for instance, preferably about 750 rpm (about 90×g) for more than about 10 minutes, for instance, and the lower layer fraction is collected. As a result of Process B, the emulsion fractions whose grain size is larger than about 5 μm and whose emulsification stability is low are removed. The conditions for these centrifugal procedures are not limited to the examples given above; any revolution rate and time can be selected as appropriate, as long as the conditions permit removal of the grain size fractions smaller than about 1 μm and those larger than about 5 μm.

The fractional purification process described above makes it possible to collect a fraction containing a high density of lipid microspheres with high emulsification stability. Of the grains in this fraction (normally about 1 to 5 μm), those having a diameter of about 1 to 3 μm are excellent in emulsification stability as demonstrated in the experimental examples given below and contain a high density of lipid microspheres with a high lipophilic drug content. This fractional purification may be conducted in any order, whether Process A precedes Process B or Process B precedes Process A.

When using a bioactive peptide as a drug, it is dissolved or suspended in water and then emulsified in the presence of neutral fats and a milk fat globule membrane of mammalian milk in the same manner as above. In this case, a protease inhibitor may be added at the same time. The protease inhibitor is not subject to limitation. Examples thereof include pepstatin, leupeptin and trapibil. The bioactive peptide may be dissolved or dispersed in a neutral buffer in place of water. Examples of neutral buffers include phosphate buffers (pH 7.0) and Tris-HCl buffers. Neutral fats, used to suspend the bioactive peptide, can be selected from those which are liquid or semi-solid at normal temperature. Examples of such neutral fats include octyldecyl triglyceride (artificial neutral fat), coconut oil and other vegetable oils, butter oil and animal or vegetable oils containing unsaturated fatty acid. When using insulin as a bioactive peptide, coconut oil serves well as a neutral fat because it excellently dissolves insulin.

When using a bioactive peptide as described above, a fat globule membrane can be used to prepare an emulsion containing the bioactive peptide, followed by fractional purification in the same manner as with a lipophilic drug to yield an emulsion fraction with excellent emulsification stability.

The fraction thus obtained can be prepared as a pharmaceutical composition by an ordinary method such as spray drying, kneading granulation or lyophilization in the presence of an appropriate filler, e.g., a synthetic or semi-synthetic polymer substance such as carboxymethyl cellulose, hydroxyethyl cellulose, hydroxypropyl cellulose, hydroxypropyl methylcellulose, polyvinyl alcohol or polyvinyl pyrrolidone, a naturally occurring polymer substance such as gum arabic, tragacanth gum or gelatin, powdered lactose, casein, microcrystalline cellulose, starch, wheat flour, dextrin or silicon dioxide for powdering the fraction. The powder thus obtained can be further prepared to have a dosage form such as tablets or hard capsules as appropriate.

Also, the fraction can be prepared as soft capsules with or without adding a thickening agent such as glycerol, since the fractional purification described above makes it possible to obtain an emulsion composition containing a lipophilic drug or bioactive peptide wherein the lipid microsphere concentration is high and the water content is very low.

When ingested in various dosage forms, the pharmaceutical composition obtained by the method of the present invention is anticipated to become emulsified in the digestive tract leading to rapid disintegration of the lipid microsphere by lipase and so on. If the disintegration of the lipid microsphere by lipase and so on proceeds rapidly, the lipophilic drug or bioactive peptide is mostly released from the lipid microsphere to the intestinal tract at one time, and no improvement in absorption such as sustained-release property by the emulsion composition containing such a drug is expected. It is therefore considered necessary to show resistance to lipase and other enzymes for retention of a sufficient level of blood concentration; the pharmaceutical composition of the present invention possesses excellent resistance to lipase.

Specifically, as stated in the experimental examples given below, when a lipase product [derived from Porcine Pancreas (a fraction containing 25% protein at 110 to 120 units/mg protein), purchased from Funakoshi Pharmaceutical Co., Ltd.], for instance, is added to a composition containing ubidecarenone as a lipophilic drug, resistance to lipase is confirmed as determined on the basis of emulsification stability, grain size distribution and electron microscopic stability. Unexpectedly, this lipase resistance can be enhanced by fractional purification by the method of the present invention; it is possible to obtain a preparation with excellent emulsification stability over time from an emulsion fraction wherein the grain size fractions larger than about 5 $\mu$m have been removed in Process B.

As stated above, when orally administered to living bodies, the pharmaceutical composition of the present invention, which has good emulsification stability and lipase resistance, shows unique drug dispersion and emulsification behavior in that it becomes emulsified very well and stably in the digestive tract and disintegrates gradually while maintaining emulsion properties against lipase and other enzymes; therefore, oral administration of the pharmaceutical composition of the present invention offers absorption improving effects such as retention of a high level of blood concentration. In fact, its utility has been confirmed in oral administration in animals (rats) as described in the experimental examples given below.

The dose of the pharmaceutical composition of the present invention thus obtained is appropriately determined according to the kind of the drug used. In the case of a composition containing ubidecarenone, for instance, as a drug, it usually contains 10 to 30% ubidecarenone therein. Generally, it is administered at about 30 mg/day in three administrations of 10 mg for adult. In the case of the preparation of the present invention, it can be administered at 5 to 15 mg/day in two to three administrations of 2.5 to 5 mg.

As stated above, the method of the present invention makes it possible to obtain an emulsion with high emulsification stability by emulsifying a lipophilic drug which is insoluble or practically insoluble in water or a bioactive peptide with a fat globule membrane in mammalian milk (e.g., bovine milk fat globule membrane) as an emulsifier and fractionally purifying the obtained emulsion grains. The pharmaceutical composition thus obtained offers improvements in the absorbability of lipophilic drugs and bioactive peptides, for example, a high level of blood concentration can be retained for a long time in oral administration because it is highly resistant to lipase. Also, the pharmaceutical composition is highly safe because the emulsifier used is derived from mammalian milk.

EXAMPLES

The present invention is hereinafter described in more detail by means of the following working examples and experimental examples, but the invention is not limited by these examples.

Example 1

100 mg of ubidecarenone (produced by Kanegafuchi Chemical Industry Co., Ltd.) as a lipophilic drug was dissolved in 1 g of triolein. To this solution 80 mg of bovine milk fat globule membrane (obtained from Chugai Pharmaceutical Co., Ltd.) was added. After diluting to a total quantity of 20 ml with a sodium phosphate isotonic buffer (pH 7.0), the mixture was homogenized at 25000 rpm for 2 minutes using a Polytron homogenizer (KINEMATICA PT10-35) and sonicated at 40 W for 2 minutes using a Branson sonifier (Branson 250) to yield an oil-in-water emulsion.

Figure 2:
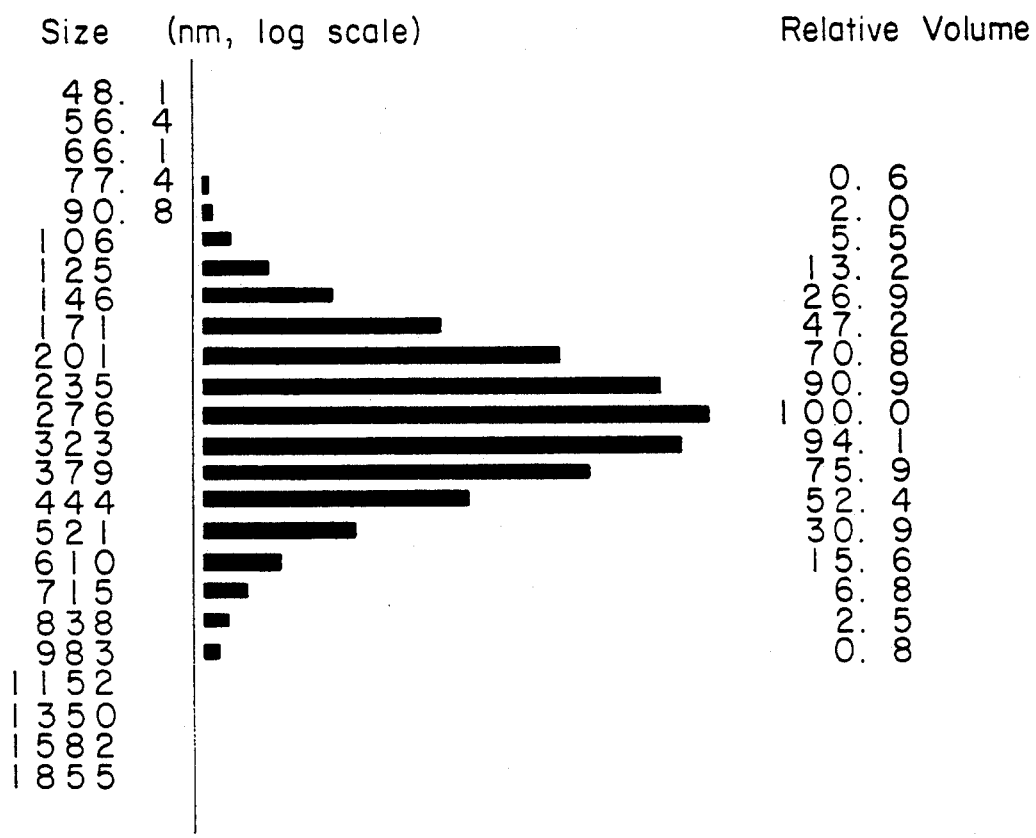
FIG. 2 shows the results of the volumetric analysis of the grain size of the lower layer fraction obtained by centrifugation at 3500 rpm (2000×g) in Example 1.

As seen from the results shown in FIG. 1, analyses of this emulsion for grain size distribution revealed the presence of emulsion grains ranging from less than 1 $\mu$m to several $\mu$m in grain diameter (no data were obtained for the grains larger than the detection limit of about 4 to 5 $\mu$m). The emulsion thus prepared was centrifuged at 3500 rpm (2000×g), whereafter the lower layer was removed and the upper layer was suspended in a sodium phosphate isotonic buffer (pH 7.0). This procedure was repeated in three cycles to remove the emulsion fractions smaller than about 1 $\mu$m in grain diameter. The grain size distribution in the removed lower layer is shown in FIG. 2.

Figure 3:
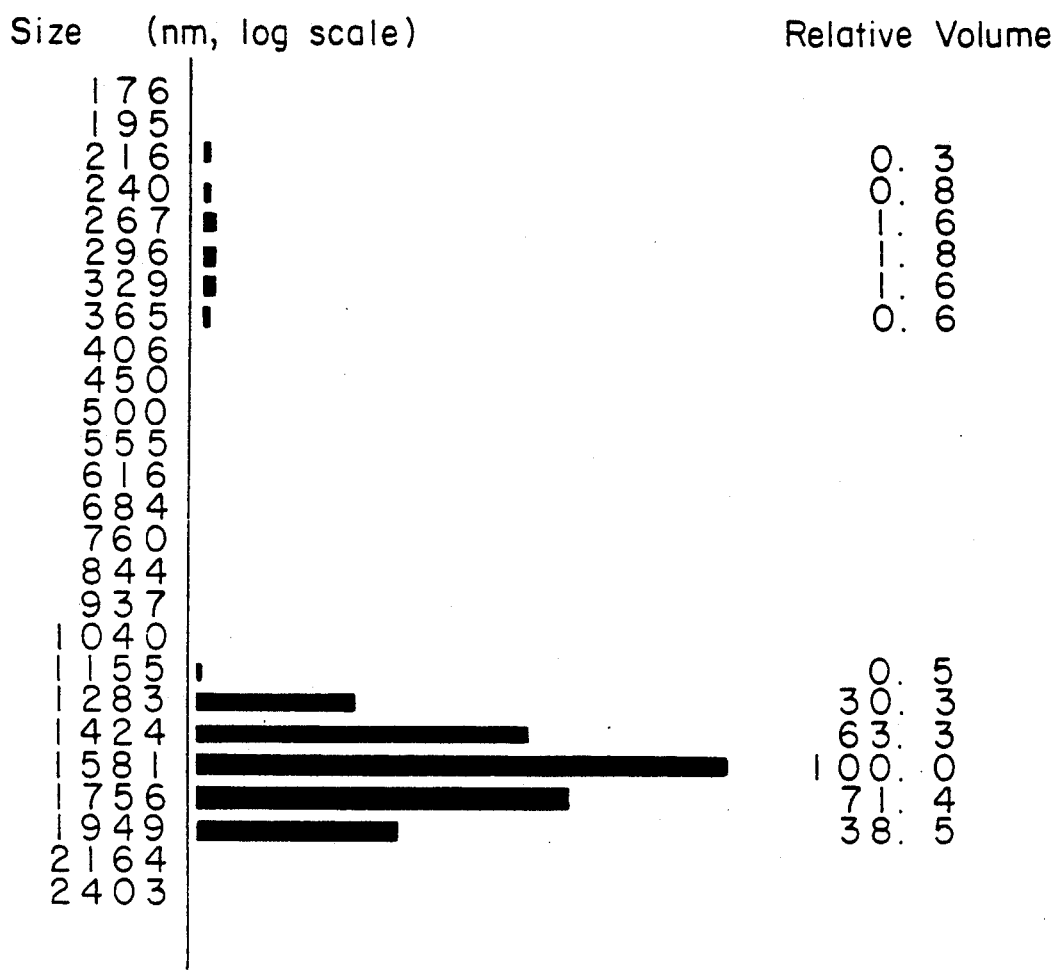
FIG. 3 shows the results of the volumetric analysis of the grain size of the lower layer fraction obtained by upper layer centrifugation at 750 rpm (90×g) after centrifugation at 3500 rpm (2000×g) in Example 1.
Figure 4:
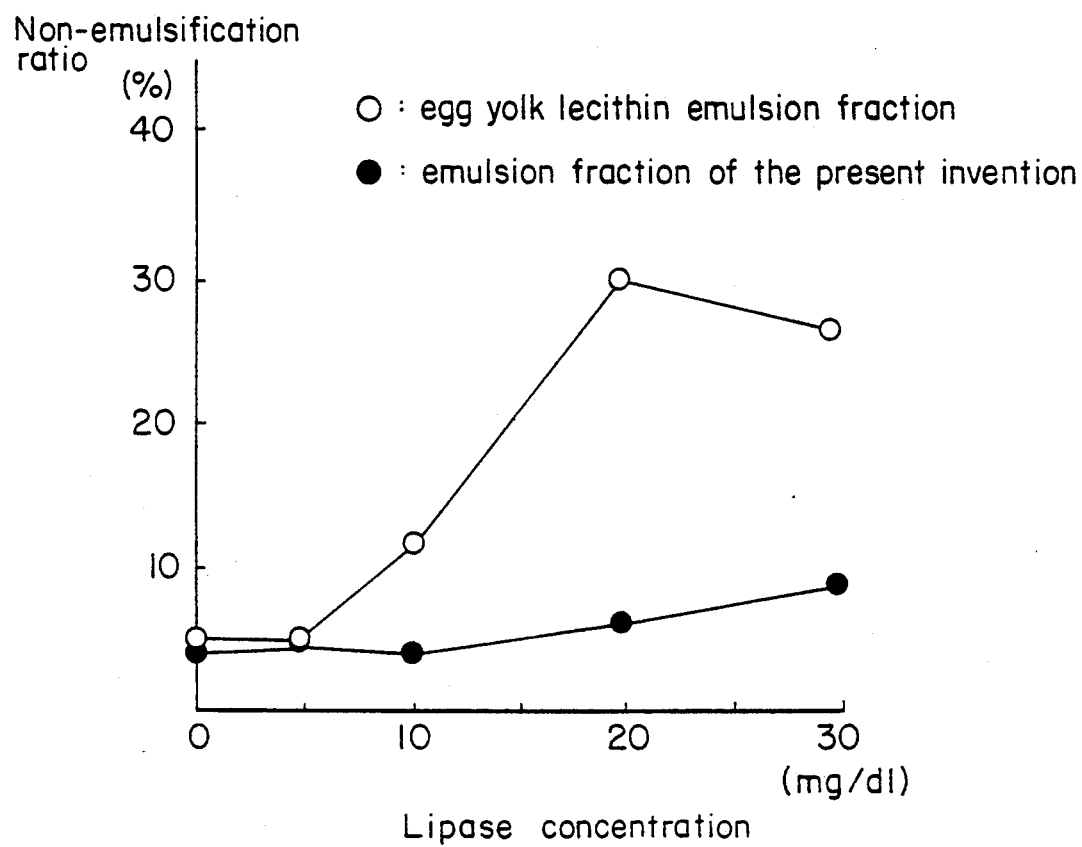
FIG. 4 shows the relationship between lipase concentration and non-emulsification ratio in Experimental Example 1.
Figure 5:
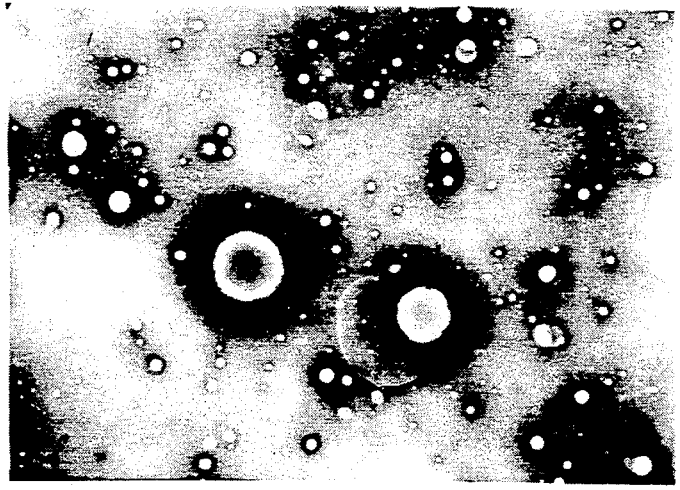
FIG. 5 is an electron micrograph showing the structure of emulsion grains in an egg yolk lecithin emulsion fraction, not treated with lipase, obtained after being kept standing for 60 minutes in Experimental Example 1.
Figure 6:
FIG. 6 is an electron micrograph showing the structure of emulsion grains in an egg yolk lecithin emulsion fraction obtained after being treated with 30 mg/dl lipase and being kept standing for 60 minutes in Experimental Example 1.
Figure 7:
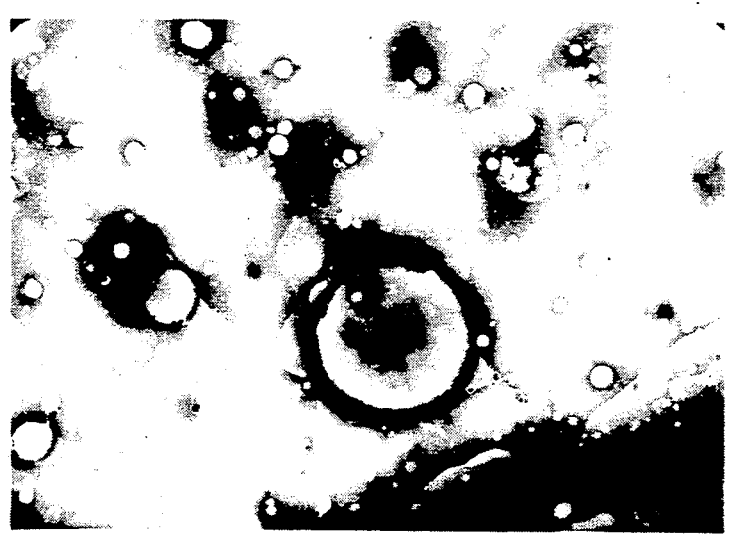
FIG. 7 is an electron micrograph showing the structure of emulsion grains in an emulsion fraction of the present invention, not treated with lipase, obtained after being kept standing for 60 minutes in Experimental Example 1.
Figure 8:
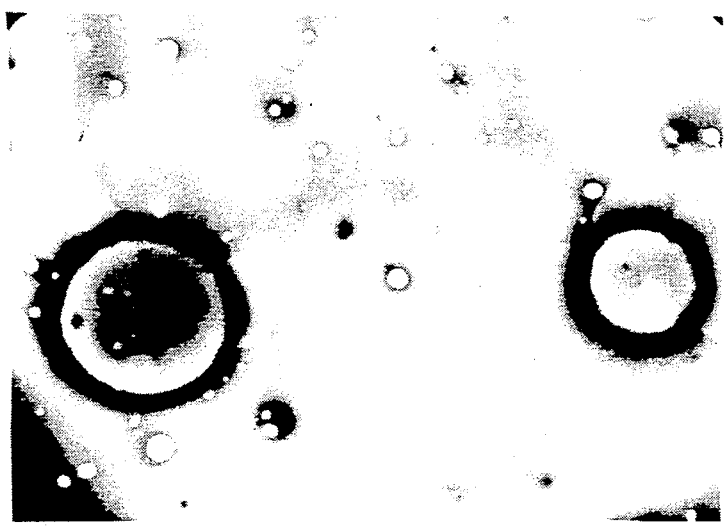
FIG. 8 is an electron micrograph showing the structure of emulsion grains in an emulsion fraction of the present invention obtained after being treated with 30 mg/dl lipase and being kept standing for 60 minutes in Experimental Example 1.

After further centrifugation at 750 rpm (90×g) for 10 minutes, the lower layer was collected to remove the emulsion fractions larger than about 5 $\mu$m in diameter. The ubidecarenone-containing emulsion fraction thus obtained (about 1 to 5 $\mu$m) was found to contain a high density of lipid microspheres about 1 to 3 $\mu$m in grain diameter as shown in FIG. 3 and have very high emulsification stability. This ubidecarenone-containing emulsion fraction was powdered by spray drying onto microcrystalline cellulose to yield a ubidecarenone-containing powder preparation. Grain size distribution was determined using the NICOMP 370/Autodilute Submicron Particle Sizer.

Example 2

500 mg of ubidecarenone (produced by Kanegafuchi Chemical Industry Co., Ltd.) as a lipophilic drug was dissolved in 5 g of triolein. To this solution 400 mg of bovine milk fat globule membrane (obtained from Chugai Pharmaceutical Co., Ltd.) was added. After diluting to a total quantity of 20 ml with a sodium phosphate isotonic buffer (pH 7.0), the mixture was homogenized at 25000 rpm for 2 minutes using a Polytron homogenizer (KINEMATICA PT10-35) and sonicated at 40 W for 2 minutes using a Branson sonifier (Branson 250) to yield an oil-in-water emulsion. The emulsion thus prepared was diluted to the maximum dilution possible, 5 fold, for instance, with a sodium phosphate isotonic buffer (pH 7.0), followed by centrifugation at 3500 rpm (2000×g), for 60 minutes, whereafter the lower layer was removed. This procedure was repeated in three cycles. Thereafter, the ubidecarence-containing emulsion fraction (about 1 to 5 $\mu$m) containing a high density of lipid microspheres about 1 to 3 $\mu$m in grain diameter and having high emulsification stability can be obtained be collecting the lower layer after centrifugation at 750 rpm (90×g). To this ubidecarenone-containing emulsion fraction glycerol was added to prepare an ubidecarenone-containing soft capsule. Grain size was determined in the same manner as in Example 1 using the NICOMP 370/Autodilute Submicron Particle Sizer.

Experimental Example 1

500 mg of ubidecarenone (produced by Kanegafuchi Chemical Industry Co., Ltd.) was dissolved in 5 g of triolein. To this solution were added 400 mg of egg yolk lecithin and 400 mg of cholesterol. After diluting with a sodium phosphate isotonic buffer (pH 7.0) to a total quantity of 20 ml, the mixture was homogenized at 25000 rpm for 2 minutes using a Polytron homogenizer (KINEMATICA PT10-35) and sonicated at 40 W for 2 minutes using a Branson sonifier (Branson 250). The oil-in-water emulsion thus obtained was centrifuged in the same manner as in Example 2 to yield an ubidecarenone-containing egg yolk lecithin emulsion fraction for control.

To this egg yolk lecithin emulsion fraction and the emulsion fraction of the present invention obtained in Example 2, lipase [derived from Porcine Pancreas (a fraction containing 25% protein at 110 to 120 units/mg protein), purchased from Funakoshi Pharmaceutical Co., Ltd.] was added to concentrations of 0, 5, 10, 20 and 30 mg/dl, and the two emulsion fractions were compared in terms of lipase resistance on the basis of emulsification stability, grain size distribution, electron micrograph and other properties. Emulsification stability was determined after the sample was enzyme treated and then kept standing at 25° C. for 24 hours. Grain size distribution and electron micrograph were determined after the sample was enzyme treated and then kept standing at 37° C. for 60 minutes.

As for emulsification stability, 10 ml of an emulsion was packed in a glass column having a diameter of 14.5 mm, which was then kept standing at room temperature in the vertical direction. A given amount of sample was taken from the lower end of the glass column at given intervals. The sample was 100 fold diluted with a sodium phosphate isotonic buffer (pH 7.0) and then kept standing for 24 hours, whereafter the total length of the emulsion and the cream length were measured. Using non-emulsification ratio (non-emulsification ratio=cream length/total length of emulsion×100) as the index (emulsification stability increases as non-emulsification ratio decreases), the emulsification stability of the emulsion was determined.

Grain size distribution was determined using the NICOMP 370/Autodilute Submicron Particle Sizer. Electron microscopic stability was determined using JEM-100CX (produced by JEOL Ltd.). As seen in FIGS. 4 through 8, in the case of the emulsion fraction of the present invention obtained in Example 2, the non-emulsification ratio was low and the emulsification condition or grain size was not significantly affected by the addition of lipase. On the other hand, in the case of the egg yolk lecithin emulsion fraction, the grain size distribution of the emulsion fraction was evidently destroyed and large size grains were formed, and a triolein layer containing dissolved ubidecarenone was formed on the emulsion surface. These findings indicate an increase in non-emulsification ratio.

Judging from this phenomenon, it is expected that the emulsion fraction of the present invention, prepared using a ubidecarenone-containing bovine milk fat globule membrane, shows resistance to lipase and retains a sufficient level of blood concentration when administered to living bodies.

Experimental Example 2

An oil-in-water emulsion before fractional purification obtained in the same manner as in Example 1 and an emulsion fraction obtained by collecting the lower layer after 10 minutes of centrifugation at 750 rpm (90×g) to remove the grains larger than about 5 μm were enzyme treated by the addition of lipase [derived from Porcine Pancreas (a fraction containing 25% protein at 110 to 120 units/mg protein), purchased from Funakoshi Pharmaceutical Co., Ltd.] to a concentration of 30 mg/dl, after which they were kept standing at 25° C. for 24 hours, and the emulsification stability was determined at given intervals.

Figure 9:
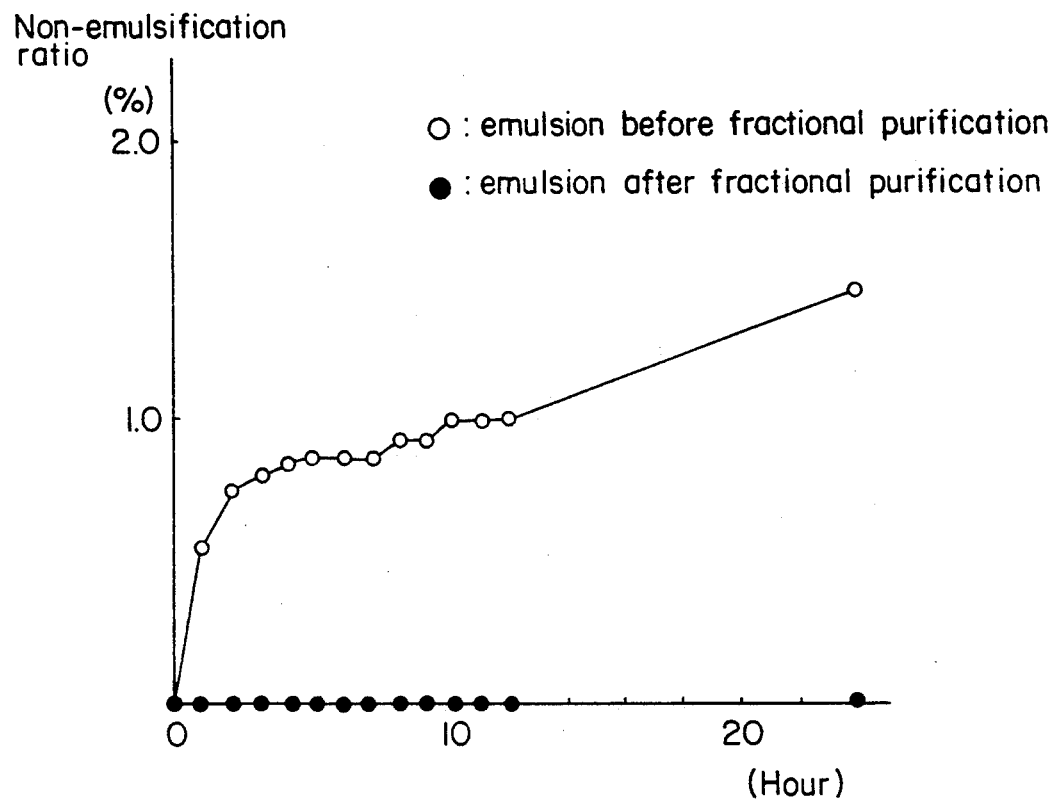
FIG. 9 compares the emulsification stabilities of the emulsions obtained before and after fractional purification in Experimental Example 2.

Emulsification stability was determined by measuring the non-emulsification ratio in the same manner as in Experimental Example 1. As seen from the results shown in FIG. 9, it was found that fractional purification improves the emulsification stability in comparison with the emulsion before fractional purification, for example, the fractionally purified emulsion shows no rise in non-emulsification ratio.

Experimental Example 3

To determine the degree of improvement in the absorbability of ubidecarenone, the emulsion fraction of the present invention obtained in Example 2 was orally administered to rats at a dose of 10 mg/kg of ubidecarenone, and serum ubidecarenone concentration was measured (subject sample). For comparison, ubidecarenone in solution in triolein was administered (control sample).

Serum ubidecarenone was assayed by high performance liquid chromatography (HPLC) using a solution in dioxane after extraction with n-hexane. HPLC conditions were: column=Finepak SIL C18T-5 (4.6×250 mm), mobile phase=methanol/ethanol (5/1), flow rate=1.5 ml/min, detection wavelength=275 nm.

Figure 10:
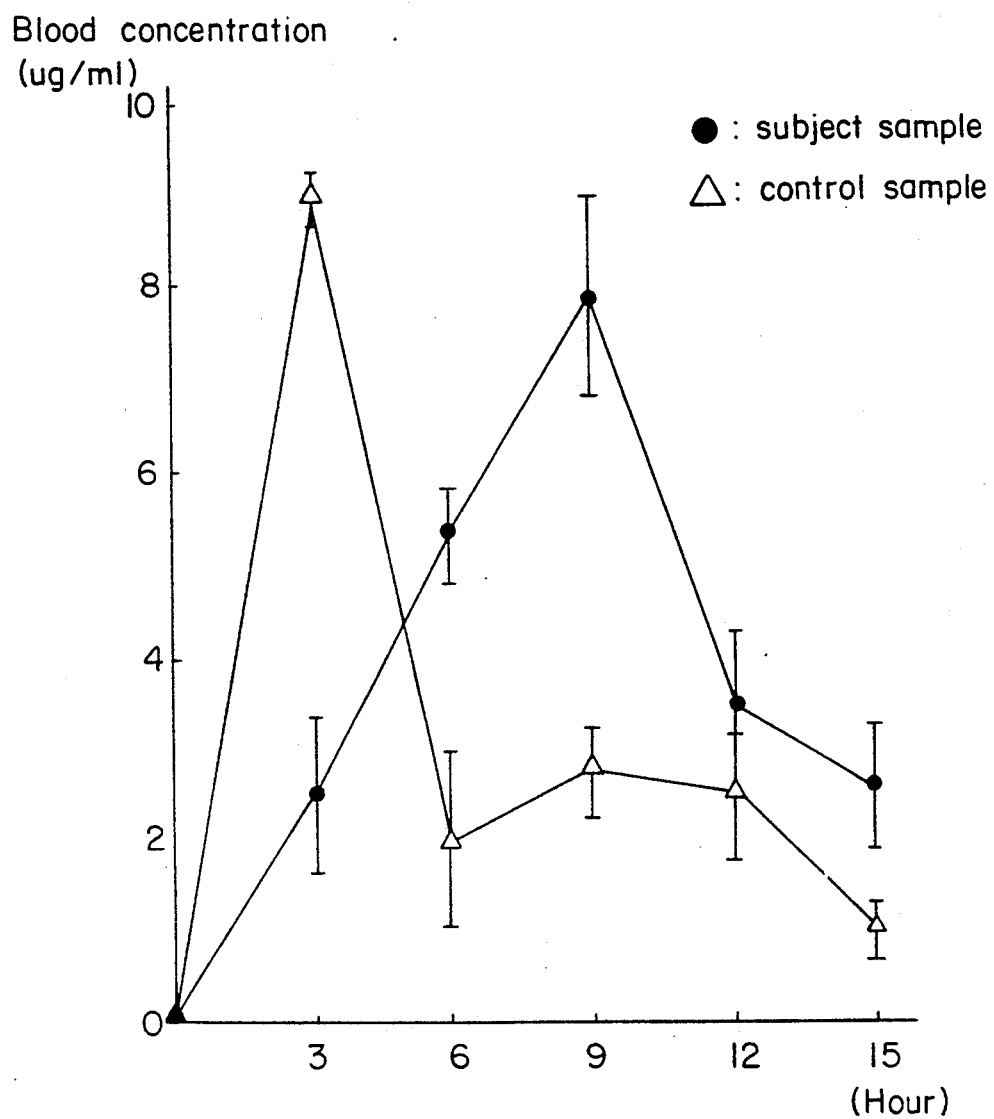
FIG. 10 shows the changes in blood concentration of an emulsion fraction of the present invention in oral administration to rats in Experimental Example 3 together with those of the control.

Changes over time of the ubidecarenone content in serum are shown in FIG. 10; it was found that a high level of serum concentration is retained for a long time by the administration of the emulsion fraction of the present invention.

What is claimed is:

1. A method for producing a pharmaceutical composition comprising the steps of emulsifying a pharmaceutically effective amount of a lipophilic drug with a fat globule membrane of mammalian milk and centrifuging it under two different sets of centrifugal conditions so as to obtain a desired grain size fraction of about 1–5 μm by fractionation; one set of centrifuging conditions being about 1500 to 2500×g for about 60 minutes or more, and the other set of said centrifuging conditions being about 50 to 150× g for about 10 minutes or more.

2. A method for producing a pharmaceutical composition according to claim 1, wherein said drug is a lipophilic drug which is insoluble or practically insoluble in water or is a bioactive peptide.

3. The method for producing a pharmaceutical composition according to claim 2, wherein said lipophilic drug is ubidecarenone.

4. A method for producing a pharmaceutical composition according to claim 1, wherein said fat globule membrane in mammalian milk is a bovine milk fat globule membrane.

5. A method for producing a pharmaceutical composition according to claim 1, wherein said grain size fraction is about 1 to 5 μm.

6. The method for producing a pharmaceutical composition according to claim 1, wherein said centrifuging is carried out by a method comprising the steps of:

Step A, removing the grain size fractions smaller than about 1 μm; and

Step B, removing the grain size fractions larger than about 5 μm.

7. The method for producing a pharmaceutical composition according to claim 6, wherein said Step A comprises centrifuging at about 1500 to 2500× g for about 60 minutes and collecting the upper layer fraction obtained in the Step A, and said Step B comprises centrifuging at about 50 to 150× g for about 10 minutes and collecting the lower layer fraction obtained in the Step B.

8. The method for producing a pharmaceutical composition according to claim 1, wherein said drug is ubidecarenone, said fat globule membrane of mammalian milk is a fat globule membrane of bovine milk and said centrifuging is carried out by a method comprising the steps of:

Step A, removing the grain size fractions smaller than about 1 μm; and

Step B, removing the grain size fractions larger than about 5 μm.

* * * * *